(12) United States Patent
Ianchulev

(10) Patent No.: US 7,556,378 B1
(45) Date of Patent: Jul. 7, 2009

(54) INTRAOPERATIVE ESTIMATION OF INTRAOCULAR LENS POWER

(76) Inventor: Tsontcho Ianchulev, 1409 N. Catalina, Los Angeles, CA (US) 90027

( * ) Notice: Subject to any disclaimer, the term of this patent is extended or adjusted under 35 U.S.C. 154(b) by 580 days.

(21) Appl. No.: 10/820,635

(22) Filed: Apr. 8, 2004

Related U.S. Application Data

(60) Provisional application No. 60/461,429, filed on Apr. 10, 2003.

(51) Int. Cl.
*A61B 3/103* (2006.01)
(52) U.S. Cl. .................. 351/212; 351/205; 351/246
(58) Field of Classification Search .................. 351/212
See application file for complete search history.

(56) References Cited

U.S. PATENT DOCUMENTS

| | | | |
|---|---|---|---|
| 4,710,193 A * | 12/1987 | Volk | 623/6.23 |
| 5,282,852 A | 2/1994 | Capetan et al. | |
| 5,329,322 A | 7/1994 | Yancey | |
| 5,455,645 A | 10/1995 | Berger et al. | |
| 5,796,463 A | 8/1998 | Bullimore | |
| 5,968,095 A | 10/1999 | Norrby | |
| 6,007,204 A | 12/1999 | Fahrenkrug et al. | |
| 6,050,687 A | 4/2000 | Bille et al. | |
| 6,439,720 B1 | 8/2002 | Graves et al. | |
| 6,609,793 B2 * | 8/2003 | Norrby et al. | 351/212 |
| 6,626,538 B1 * | 9/2003 | Arrowsmith | 351/246 |
| 6,634,751 B2 | 10/2003 | Turner et al. | |
| 7,490,938 B2 * | 2/2009 | Latkany | 351/177 |
| 2004/0156014 A1 * | 8/2004 | Piers et al. | 351/168 |
| 2004/0167622 A1 * | 8/2004 | Sunalp et al. | 623/6.12 |

OTHER PUBLICATIONS

Aramberri, "Intraocular lens power calculation after corneal refractive surgery: Double-K method," J Cataract Refract Surg 29:2063-2068 (Nov. 2003).

Argento et al., "Intraocular lens power calculation after refractive surgery," J Cataract Refract Surg 29:1346-1351 (Jul. 2003).

Binkhorst, "Power of the Pre-Pupillary Pseudoshakos," B.J.O. 56:332-37 (1972).

Binkhorst, "The optical design of intraocular lens implants," Ophthalmic Surg 6(3):17-31 (1975).

Chen et al., "Analysis of intraocular lens power calculation in post-radial keratotomy eyes," J Cataract Refract Surg 29:65-? (Jan. 2003).

Colenbrander, "Calculation of the Power of an Iris-Clip Lens for Distance Vision," Br. J. Ophthal. 57:735-40 (1973).

Cua et al., "Intraocular lens calculations in patients with corneal scarring and irregular astigmatism," J Cataract Refract Surg 29:1352-1357 (Jul. 2003).

(Continued)

*Primary Examiner*—Jessica T Stultz
(74) *Attorney, Agent, or Firm*—Fish & Richardson P.C.

(57) ABSTRACT

Apparatus for performing intraocular implant surgery, including surgical apparatus for performing intraocular implant surgery, an autorefraction device associated with the surgical apparatus, wherein the autorefraction device is configured to perform autorefraction on the aphakic eye to provide one or more aphakic refraction measurements, and a processor connected to the autorefraction device, wherein the processor is configured to process the aphakic refraction measurements and provide the user of the apparatus with information regarding the power of the intraocular lens.

11 Claims, 2 Drawing Sheets

OTHER PUBLICATIONS

Feiz et al., "Intraocular Lens Power Calculation After Laser In Situ Keratomileusis for Myopia and Hyperopia—A Standardized Approach," Cornea 20(8);792-797 (2001).

Feordorov et al., "Estimation of optical power of the intraocular lens," Vestn. Oftamol 80(4):27-31 (1967).

Gernet, "IOL calculation according to Gernet and the GOW 70 PC programme," Abstract from Opthalmologe 98:873-876 (2001).

Gimbel et al., "Accuracy and predictability of intraocular lens power claculation after laser in situ keratomileusis," J Cataract Refract Surg 27:571-576 (Apr. 2001).

Gimbel et al., "Accuracy and predictability of intraocular lens power calculation after photorefractive keratectomy," J Cataract Refract Surg 26:1147-1151 (Aug. 2000).

Hamilton et al., "Cataract surgery in patients with prior refractive surgery," Current Opinion in Ophthalmology 14:44-53 (2003).

Harvey et al., "Reproducibility and accuracy of measurements with a hand held autorefractive in children," Journal of Ophthalomology 81:941-948 (1997).

Hoffer, "Calculating Corneal Power After Refractive Surgery," Cataract & Refractive Surgery Today 4(4):23-25 (Apr. 2004).

Hoffer, "Mathematics and computers in intraocular lens calculation," Am Intra-Ocular Implant Soc J 1(1):4-5 (1975).

Holladay et al., "A three-part system for refining intraocular lens power calculations," J Cataract Refract Surg 14:17-24 (Jan. 1988).

Hunt et al., "Evalution of the measurement of refractive error by the PowerRefractor: a remote, continuous and binocular measurement system of oculomotor function," Br J Opthalmol 87:1504-1508 (2003).

Ianchulev, "Method for Intraoperative Refractive IOL Calculation," Poster Presentation at Ophthalmology Conference (Apr. 2004).

Isenberg et al., "Use of the HARK Autorefractor in Children," American Journal of Ophthalmology 131(4):438-441 (2001).

Kora et al., "Intraocular lens power calculation for lens exchange," J Cataract Refract Surg 27:543-548 (Apr. 2001).

Liang et al., "Comparison of Measurements of Refractive Errors Between the Hand-held Retinomax and On-table Autorefractors in Cyclopleged and Noncyclopleged Children," American Journal of Ophthalmology 136(6):1120-1128 (Dec. 2003).

Liang et al., "Comparison of the handheld Retinomax K-Plus 2 and on-table autokeratometers in children with and without cycloplegia," J Cataract Refract Surg 30:670-674 (Mar. 2004).

Nemeth et al., "Optical and ultrasound measurement of axial length and anterior chamber depth for intraocular lens power calculation," J Cataract Refract Surg 29:85-88 (Jan. 2003).

Olsen, "Theoretical approach to intraocular lens calculation using Gaussian optics," J Cataract Refract Surg. 13:141-145 (Mar. 1987).

Olsen, "Theoretical, computer-assisted prediction versus SRK prediction of postoperative refraction after intraocular lens implantation," J Cataract Refract Surg 13:141-145 (Mar. 1987).

Orr et al., "Manifest Refraction Versus Autorefraction for Patients with Subfoveal Choroidal Neovascularization," Investigative Ophthalmology & Visual Science 42:(2):447-451 (Feb. 2001).

Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).

Raj et al., "Objective autorefraction in posterior chamber pseudophakia," British Journal of Ophthalmology 74:731-733 (1990).

Raj et al., "Clinical evaluation of automated refraction in anterior chamber pseudophakia," British Journal of Ophthalmology 75:42-44 (1991).

Sanders et al., "Comparison of the SRK™ formula and other second generation formulas," J Cataract Refract Surg 14:136-141 (Mar. 1988).

Sanders et al., "Comparison of the SRK/T formula and other theoretical and regression formulas," J Cataract Refract Surg 16:341-346 (May 1990).

Siganos et al., "Autorefractometry after laser in situ keratomileusis," J Cataract Refract Surg 29:133-137 (Jan. 2003).

Suto et al., "Adjusting intraocular lens power for sulcus fixation," J Cataract Refract Surg 29:1913-1917 (Oct. 2003).

Thall et al., Linear Regression Software for Intraocular Lens Implant Power Calculation, American Journal of Ophthalmology 101:597-599 (May 1986).

Thompson et al., "A New Posterior Chamber Intraocular Lens Formula for Axial Myopes," Ophthalmology 91(5):484-488 (May 1984).

Tromans et al., "Accuracy of intraocular lens power calculation in paediatric cataract surgery," Br J Ophthalmol 85:939-941 (2001).

Zaldivar et al., "Intraocular lens power calculations in patients with extreme myopia," J Cataract Refract Surg 26:668-674 (May 2000).

Collection of abstracts and citations of publications.

\* cited by examiner

INTRAOPERATIVE ESTIMATION OF INTRAOCULAR LENS POWER

CROSS-REFERENCE TO RELATED APPLICATION

This application claims priority to U.S. Provisional Application Ser. No. 60/461,429, filed on Apr. 10, 2003.

TECHNICAL FIELD

This invention relates to methods and apparatus for selecting the power of an intraocular lens to be implanted into an eye.

BACKGROUND

The history of intraocular lens implantation dates back to 1949 when an initial attempt to replace a diseased lens with an artificial one resulted in a poor outcome with an error of −24.0 diopter (D). Nevertheless, this set the stage for continuous advances in the field of opthalmology, leading to the common practice of "standard-of-care" lens implantation we see today. The technology of cataract surgery has witnessed an impressive development through constant innovation of surgical technique and instrumentation, lens material and design, and just as importantly, ever improving methodology for calculating and predicting the power of the lens implant necessary to achieve desired postoperative refractive outcome. In the 1960s Fyodorov was the first scientist to publish a formula for predicting the power of the intraocular lenses (IOLs) based on geometrical optics incorporating two very important preoperative anatomical parameters of the ocular system—the A-scan derived axial length of the eye and keratometry measurements of the cornea. Feodorov S N, Kolinko A L, *Estimation of optical power of the intraocular lens*. Vestn. Oftamol; 80(4):27-31 (1967). Colenbrander published the first formula written in English in 1973. Colenbrander, *Calculation of the Power of an Iris-Clip Lens for Distance Vision*, Br. J. Ophthal. 57:735-40 (1973). Many further improvements followed these pioneering efforts. Binkhorst described a derivative formula in the 1970s. Binkhorst R D., *The optical design of intraocular lens implants*. Ophthalmic Surg 1975; 6(3):17-31. Binkhorst, *Power of the Pre-Pupillary Pseudoshakos*, B. J. O. 56:332-37, (1972)). Modifications of the Colenbrander formula were implemented by Dr. Hoffer with further improvement of accuracy across the different axial length ranges. Hoffer K J. *Mathematics and computers in intraocular lens calculation*. Am Intra-Ocular Implant Soc J 1975; 1(1):4-5). In 1980, Sanders, Retzlaff and Kraff derived a regression formula which has sustained many subsequent updates and modifications. Further refinements were achieved with the second generation formulas which had better precision over a wider range of anatomic parameters, but all used axial length and corneal curvature (keratometry) as the main predictive variable in their models. Sanders, J. Retzlaff & M. C. Kraff, *Comparison of the SRK II Formula and the Other Second Generation Formulas*, J. Cataract & Refractive Surg. 14(3):136-41 (1988). Olsen, T., *Theoretical Approach to IOL Calculation Using Gaussian Optics*, J. Cataract & Refractive Surg. 13:141-45 (1987). Holladay, T. C. Praeger, T. Y. Chandler & K. H. Musgrove, *A Three-Party System for Refining Intraocular Lens Power Calculations*, J. Cataract & Refractive Surg. 14:17-24 (1988). J. T. Thompson, A. E. Maumenee & C. C. Baker, *A New Posterior Chamber Intraocular Lens Formula for Axial Myopes*, Ophthal. 91:484-88 (1984). Various improvements in making preoperative anatomic-based estimates of IOL power have been described in the patent literature (e.g., U.S. Pat. Nos. 6,634,751, 5,968,095, and 5,282,852).

The shortcomings of current technology are multifold. Even in the ideal and most simplified clinical setting, about 10-20% of patients remain with at least 1.0 diopter refractive error after surgery. In about 3-5% of cases this residual can be as high as 2 diopters. Also, traditional IOL estimation techniques based on axial length and corneal curvature produce even greater inaccuracy when the cataract surgery is done after vision correcting refractive surgery (e.g., Lasik, Lasek, wavefront and other similar corrective procedures). In this setting, a larger residual error can result (e.g., more than about 80% of such cases have about 1-1.5 diopter error). Reliance on anatomic measurements is even more problematic for a patient whose eye shape is at the extreme end of the range of an anatomic parameter.

Autoretinoscopy has been traditionally used for determination of the optical state of the ocular system in an office visit. In this office setting, autoretinoscopy is used as an objective measurement to guide the subjective testing and estimation of the power for corrective eye glass prescription. In this setting, an autorefractor based on the principle of automated retinoscopy, is used with the eye in the phakic state (i.e., with the native lens in its native position). A number of widely available autoretinoscopes are employed with the patient in a sitting position in front of the apparatus.

In recent years, very significant advances have been made in IOL surgical techniques and instrumentation (e.g., micro-incision techniques for quick and controlled cataract surgery), but IOL power has continued to be estimated preoperatively using anatomic measurements.

SUMMARY

The problems associated with current methods for IOL power estimation lie in the reliance on preoperative measurements, e.g., corneal curvature and axial length. These parameters can change significantly after the eye has been manipulated. For example, the curvature of the cornea and its optical properties change after incisions and intraocular procedures. Current models extrapolate the effective lens position of the implant through lens-associated constants, such as the A-constant, which are inherent to the specific lens design, but not to the particular anatomy of each eye, and therefore not individually customized to each surgical case. The current methods, because they only approximate the optical deficiency of the eye after lens extraction, lead to residual errors in lens power.

In a first aspect, the invention features a method for selecting the power of an intraocular lens, comprising extracting the native lens, performing autorefraction on the aphakic eye to provide one or more aphakic refraction measurements, and determining the power of the intraocular lens from the one or more aphakic refraction measurements.

Preferred implementations of this aspect of the invention may incorporate one or more of the following. The autorefraction may be performed with the patient in the same position in which the native lens was extracted. The position of the patient may be the supine position. The method may be used for patients that have previously undergone vision correcting refractive surgery. Determining the power of the intraocular lens may comprise using a predictive model that is an empirically derived relationship between the autorefraction measurements and the power of the intraocular lens. Determining the power of the intraocular lens may comprise using a predictive model that is a theoretically derived relationship between the autorefraction measurements and the power of the intraocular lens. The native lens may be extracted using a surgical microscope and the autorefraction may be performed using an autorefraction device configured to be moved into place for making autorefraction measurements following extraction of the native lens using the surgical microscope. The autorefraction may comprise making a plurality of autorefraction measurements and averaging the measurements. Determining the power of the intraocular lens may comprise determining the power from the one or more autorefractive measurements and from other parameters. The other parameters may include preoperative anatomic measurements of the eye. They may also include one or more of the following: intraocular pressure, intraoperative axial length, intraoperative keratometry, preoperative keratometry, preoperative axial length, intraoperative anterior chamber depth, or preoperative anterior chamber depth.

In a second aspect, the invention features apparatus for performing intraocular implant surgery, comprising surgical apparatus for performing intraocular implant surgery, an autorefraction device associated with the surgical apparatus, wherein the autorefraction device is configured to perform autorefraction on the aphakic eye to provide one or more aphakic refraction measurements, and a processor connected to the autorefraction device, wherein the processor is configured to process the aphakic refraction measurements and provide the user of the apparatus with information regarding the power of the intraocular lens.

Preferred implementations of this aspect of the invention may incorporate one or more of the following. The apparatus may further comprise a display for providing the user of the apparatus with the information regarding the power of the intraocular lens. The autorefraction device may be attached to or integrated with the surgical apparatus. The surgical apparatus may be a surgical microscope and the autorefraction device may comprise an autorefraction device configured to be moved into place for making refraction measurements following extraction of the native lens using the surgical microscope. The autorefraction device may be a portable autorefraction device that is used while a patient is in the supine position following surgical extraction of the lens. The autorefraction device may comprise a retinoscope. The autorefraction device may comprise a wavefront-based autorefraction device. The autorefraction device may comprise apparatus for measuring the aphakic dioptric state, the deficiency of the ocular system, or both the aphakic dioptric state and the deficiency of the ocular system. The autorefraction device may comprise or work in combination with an external lens, contact lens, intraocular lens, or other component with refractive or medium properties positioned along the optical axis along an autorefraction measurement trajectory. The surgical apparatus may comprise a surgical microscope that includes an ocular piece or display for centration and positioning and a toggle for XYZ movement, and wherein the autorefraction device may be positioned and configured so that movement of the toggle can adjust the position of the autorefraction device relative to the eye.

Among the many advantages of the invention (some of which may be achieved only in some of its various aspects and implementations) are the following: Greater precision is possible in estimating required IOL power, and thus there is less residual refractive error. It is possible to achieve reductions in the complexity and cost associated with IOL implantation surgery (e.g., it may be possible to eliminate the need for expensive equipment such as an A-scan biometry device and a keratometer, as well as the need for a separate pre-operative patient visit at which pre-operative eye measurements are made). The invention makes it possible to break away from the conventional preoperative anatomical approaches derived from Feodorov's original work in 1967. New refractive measurement technology can be used to predict the power of the intraocular lens. Anatomic parameters such as preoperative axial length and keratometry are no longer essential to the process of estimating the power of the intraocular lens (but these parameters, as well as others, may, in some implementations, be used in combination with the intraoperative autorefraction measurements). Relying on intraoperative measurement of the aphakic refractive state of the eye after lens extraction has the advantage that it measures the optical deficiency of the ocular system without the confounding interference of the native lens. Modern retinoscopy technology can be adapted to cataract surgery immediately after extraction of the cataract, when the eye is transiently aphakic; in this state, the cornea is the primary refractive medium and the optical system of the eye is in a unique state of non-interference by the lenticular optical component. When an autorefraction or other form of retinoscopy is done before a lens is implanted, the measurements are primed to correlate closely with the missing intraocular lens power. From these measurements the surgeon one can derive, correlate and calculate the parameters of the lens to be inserted. The method can be used solely for the purposes described or in combination with other ocular measurements and parameters obtained prior or during surgery to optimize accuracy and precision.

Other features and advantages of the invention will be found in the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
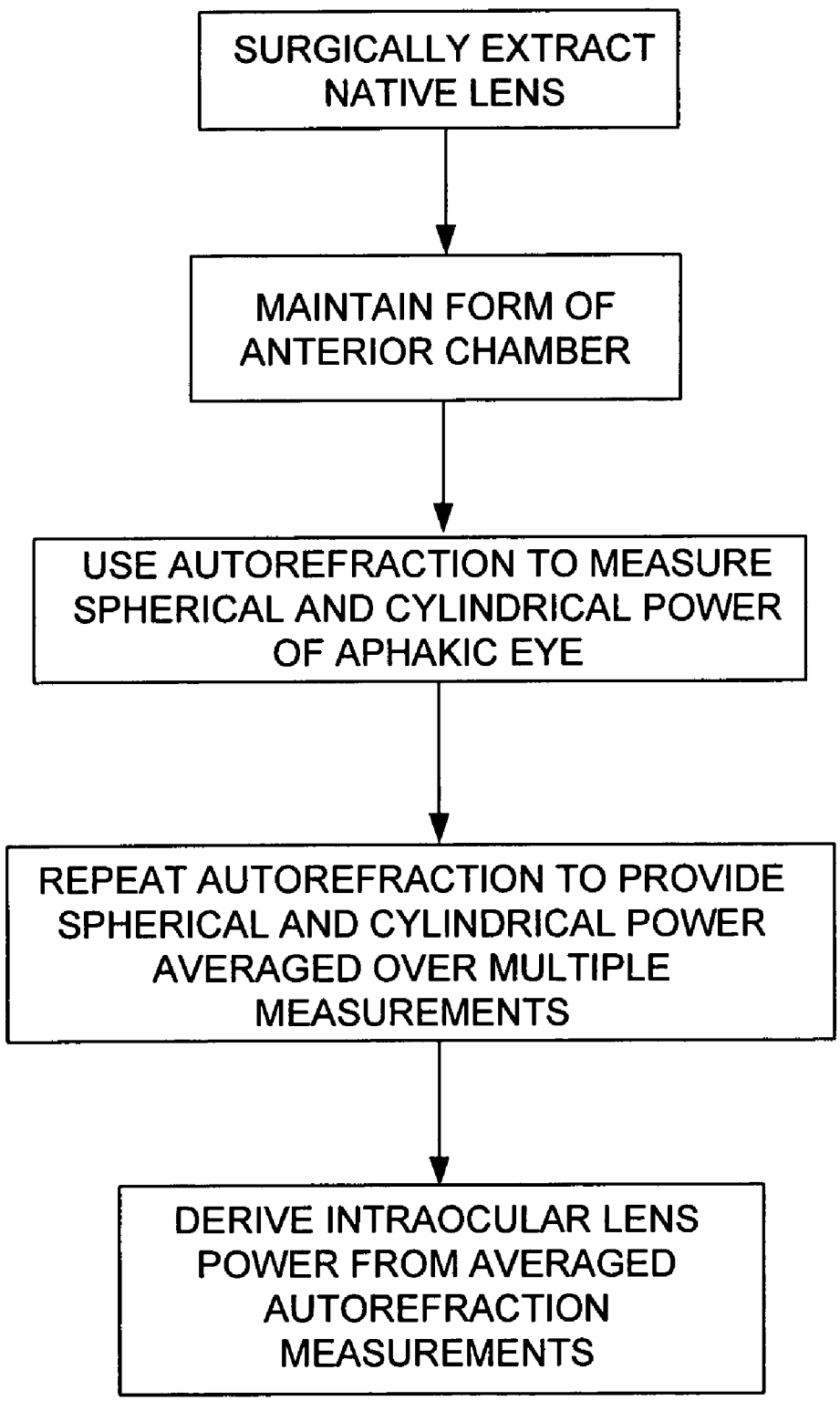
FIG. 1 is flow chart of steps in one implementation of the invention.

FIG. 1 shows the process followed in one implementation of the invention. Any surgical technique for lens extraction may be used, including such conventional techniques as phacoemulsification or extracapsular cataract extraction. After the lens is extracted from the eye and all particulate lens material is removed, the anterior chamber is maintained formed with intraocular fluid or viscoelastic. The eye is then centered and an autorefracting device is used to obtain a refractive reading of the aphakic eye (i.e., the eye with the lens removed). While any autorefractor can be used across a wide range of possible vertex distances, one possible implementation is to use an autorefractor with a vertex distance of 13.75 mm, and to take an average of multiple autorefraction measurements. Autorefraction provides a spherical and a cylindrical power measurement.

The power of the intraocular lens can be derived from the refraction measurements. One possible method for deriving the intraocular lens power is to use an empirically derived relationship, which could be called a predictive IOL model, that relates the refraction measurements to the IOL power.

This can be done, for example, by first calculating the aphakic spherical equivalent of the refraction measurements from the standard formula:

Spherical Equiv=Measured Spherical Power+½ Measured Cylindrical Power, wherein Spherical Equiv is the aphakic spherical equivalent, Measured Spherical Power is the average of the spherical power measurements made using autorefraction, and Measured Cylindrical Power is the average of the cylindrical power measurements made using autorefraction. Next, the following empirically derived relationship may be used to relate the aphakic spherical equivalent to the IOL power:

IOL Power=$A+c+b$*(Spherical Equiv), wherein A is the lens specific constant (and depends on the type of intraocular lens being implanted), c is an empirically derived constant, and b is the empirically derived linear correlation coefficient.

The two empirically derived coefficients c, b may be derived using a statistical regression analysis of data relating IOL power to autorefraction measurement of the spherical equivalent. For example, the regression analysis may be performed on data collected from a large population of patients (e.g., one hundred patients). For each patient, the data comprise the IOL Power selected using conventional preoperative measurements and the spherical equivalent from an intraoperative autorefraction.

Other relationships between the refraction measurements and the IOL power may also be used, and the necessary constants and coefficients derived either empirically or theoretically. One alternative, of course, is to simply combine the two formulas as follows:

IOL Power=$A+c+b$*(Measured Spherical Power+½ Measured Cylindrical Power),

Varying the vertex distance of autorefraction or modifying the optical media along the optical path (e.g., by inserting a different material into the anterior chamber of the eye, or by placing a temporary lens in or near the eye) can alter the parametric variables of the relationship.

In some implementations, the above formulation can be improved with additional variables to achieve better precision. Parameters such as intraocular pressure, intraoperative axial length, intraoperative keratometry, preoperative keratometry, preoperative axial length, intra and preoperative anterior chamber depth can be used as supplementary correlates in the predictive model, in order to refine the IOL power. For example, the following relationship could be used:

IOL Power=$A+c+b$*(Spherical Equiv)+$d$*(Axial Length)+$f$*(Average Keratometry)+$g$*(Intraoperative Pressure)

In one implementation, both the surgery and the autorefraction are performed using standard available equipment. A standard surgical microscope is used for extraction of the native lens, and a standard portable autorefraction device (e.g., a Nikon Retinomax) is used for autorefraction. Both procedures may be performed while the patient remains in the same supine position. The refraction measurements are read from the autorefraction device, and the IOL power is calculated using a formula such as one of those given above.

Figure 2:
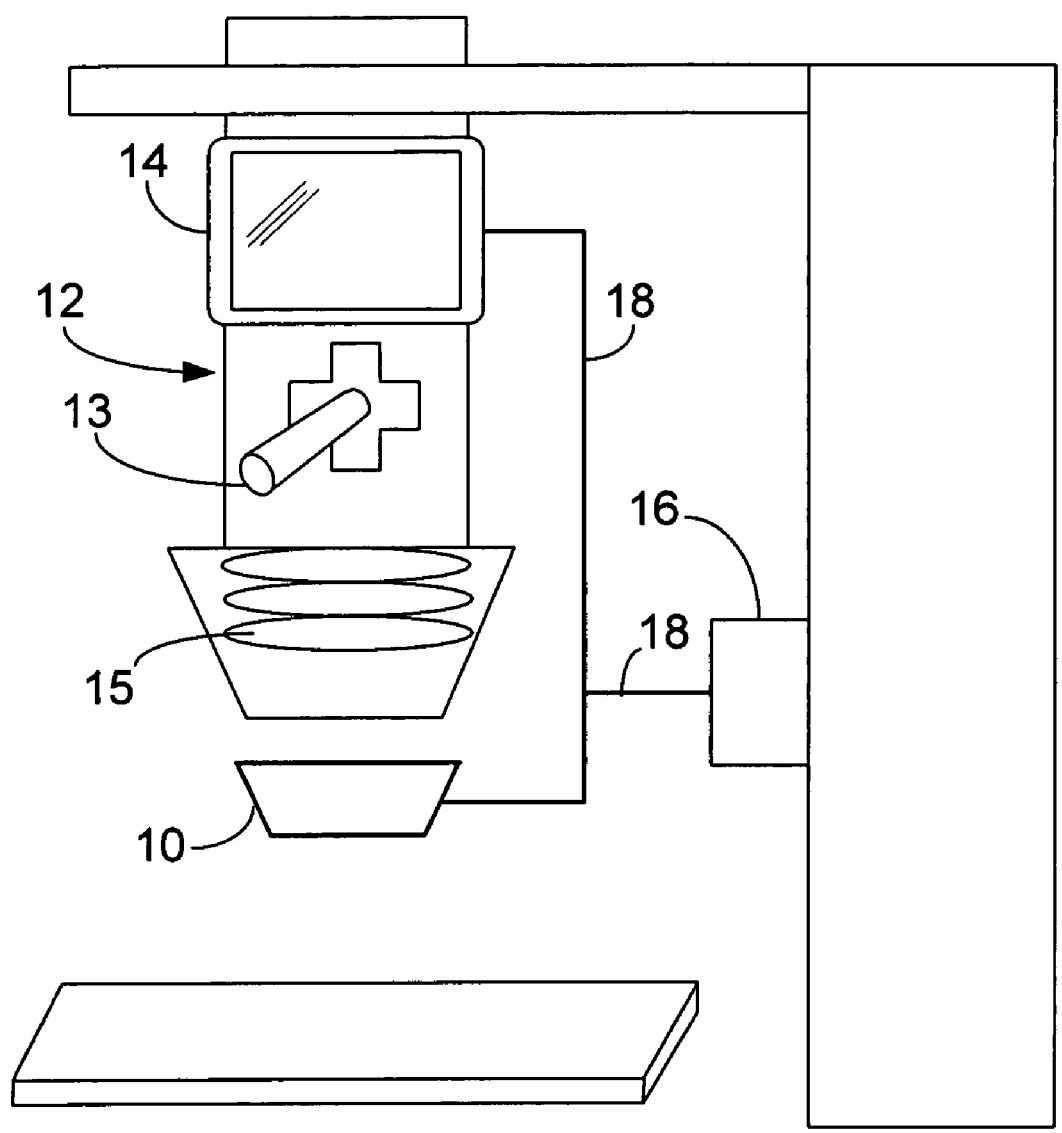
FIG. 2 is a diagrammatic view of apparatus implementing the invention in pone possible manner.

FIG. 2 shows another possible implementation in which specially designed equipment is used. An autorefraction retinoscope unit 10 is attached to the exterior of an ophthalmic surgical microscope 12. The surgical microscope in this implementation has its own display for centration and visualization. A toggle control 13 (and/or a pedal control) is provided for XYZ centration of the microscope and the retinoscope unit. The microscope has the usual lens array 15. The autorefraction unit can be a conventional automated retinoscopic apparatus of the type conventionally used to measure the dioptric deficiency and optical state of the phakic eye. The retinoscopic apparatus would be configured to operate with the patient in the supine position, intraoperatively, and to be moved out of the way of the microscopic surgical device when not in use, but configured so that its position and orientation is adjustable using the toggle control 13. A display unit 14 is integrated with the autorefraction unit 10 and also attached to the surgical microscope 12. The display unit presents the results of the IOL power determination. A processing unit 16 is electrically connected to the autorefraction unit and the display. Cables 18 make the electrical connections between the autorefraction unit 10, display unit 14, and processing unit 16. The processing unit receives measurement data from the autorefraction unit, and uses a predictive model (e.g., one of those described by the above formulas) to calculate the IOL power for display on the display unit.

An alternative to the arrangement shown in FIG. 2 would be to have the autorefraction unit, display unit, and processing unit fully integrated into the ophthalmic surgical microscope. For example, the same display unit can serve both for centration and visualization during surgery and for controlling and displaying results from the autorefraction unit and processing unit during IOL power determination.

The equipment of FIG. 2 or alternative implementations may be used to perform the eye surgery, to make the intraoperative refraction measurement, and to calculate the IOL power for achieving the desired emmetropia or postoperative refraction.

Many other implementations of the invention other than those described above are within the invention, which is defined by the following claims. For example, as earlier noted, completely separate surgical and autorefraction equipment may be used (e.g., with the microscope moved away, and the autorefraction equipment moved into place), and the IOL measurement may be calculated from the refraction measurements without using a special processor or display unit. Autorefraction may also be used after the intraocular lens is implanted (pseudophakic eye), to confirm whether a satisfactory choice has been made for the IOL power. If the autorefraction shows a residual error, the surgeon could immediately remove the implanted lens, and substitute another. Various types of autorefraction may be used to make the intraoperative refraction measurement of the aphakic eye.

The invention claimed is:

1. A method for selecting the power of an intraocular lens, comprising extracting the native lens;
    performing autorefraction on the aphakic eye to provide one or more aphakic refraction measurements;
    determining the power of the intraocular lens from the one or more aphakic refraction measurements,
    wherein the power is a measurement of the spherical correction of the lens,
    wherein the autorefraction is performed using an autorefraction device configured to be moved into place for making autorefraction measurements following extraction of the native lens, and
    wherein the determining the power of the intraocular lens comprises using a predictive model that provides a relationship between the autorefraction measurements and the power of the intraocular lens.

2. The method of claim 1 wherein the autorefraction is performed with the patient in substantially the same position in which the native lens was extracted.

3. The method of claim 2 wherein the position of the patient is the supine position.

4. The method of claim 1 wherein the method is used for patients that have previously undergone vision correcting refractive surgery.

5. The method of claim 1 wherein the predictive model is an empirically derived relationship between the autorefraction measurements and the power of the intraocular lens.

6. The method of claim 1 wherein the predictive model is a theoretically derived relationship between the autorefraction measurements and the power of the intraocular lens.

7. The method of claim 1 wherein the native lens is extracted using a phacoemulsification surgical technique.

8. The method of claim 1 wherein the autorefraction comprises making a plurality of autorefraction measurements and averaging the measurements.

9. The method of claim 1 wherein determining the power of the intraocular lens comprises determining the power from the one or more autorefractive measurements and from other parameters.

10. The method of claim 9 wherein the other parameters include preoperative anatomic measurements of the eye.

11. The method of claim 9 wherein the other parameters include one or more of the following: intraocular pressure, intraoperative axial length, intraoperative keratometry, preoperative keratometry, preoperative axial length, intraoperative anterior chamber depth, or preoperative anterior chamber depth.

* * * * *